US010492811B2

(12) United States Patent
Slater

(10) Patent No.: US 10,492,811 B2
(45) Date of Patent: Dec. 3, 2019

(54) ROTATABLE ENDOSCOPIC INSTRUMENT

(71) Applicant: Slatr Surgical Holdings LLC, Fort Lauderdale, FL (US)

(72) Inventor: Charles R. Slater, Fort Lauderdale, FL (US)

(73) Assignee: Slatr Surgical Holdings LLC, Ft. Lauderdale, FL (US)

(*) Notice: Subject to any disclaimer, the term of this patent is extended or adjusted under 35 U.S.C. 154(b) by 87 days.

(21) Appl. No.: 15/499,573

(22) Filed: Apr. 27, 2017

(65) Prior Publication Data

US 2018/0310985 A1 Nov. 1, 2018

(51) Int. Cl.
*A61B 17/29* (2006.01)
*A61B 18/00* (2006.01)
*A61B 17/00* (2006.01)

(52) U.S. Cl.
CPC .... *A61B 17/29* (2013.01); *A61B 2017/00367* (2013.01); *A61B 2017/2905* (2013.01); *A61B 2017/2911* (2013.01); *A61B 2017/2924* (2013.01); *A61B 2017/2929* (2013.01); *A61B 2018/0091* (2013.01); *A61B 2018/00202* (2013.01)

(58) Field of Classification Search
CPC ........... A61B 2018/00166; A61B 2018/00172; A61B 2018/00178; A61B 2018/00196; A61B 2018/0091; A61B 2018/00916; A61B 2018/00934; A61B 2018/0946; A61B 2018/00952
See application file for complete search history.

(56) References Cited

U.S. PATENT DOCUMENTS

| | | | |
|---|---|---|---|
| 4,861,340 A | 8/1989 | Smith et al. | |
| 5,282,806 A | 2/1994 | Haber et al. | |
| 5,397,310 A * | 3/1995 | Chu | A61M 39/0613 604/158 |
| 5,577,654 A | 11/1996 | Bishop | |
| 5,683,385 A * | 11/1997 | Kortenbach | A61B 18/1445 439/909 |
| 5,779,646 A | 7/1998 | Koblish et al. | |
| 5,954,731 A * | 9/1999 | Yoon | A61B 17/062 606/139 |
| 5,967,997 A | 10/1999 | Turturro et al. | |
| 5,995,875 A * | 11/1999 | Blewett | A61B 18/1477 606/41 |

(Continued)

*Primary Examiner* — Ronald Hupczey, Jr.
(74) *Attorney, Agent, or Firm* — Gordon & Jacobson, P.C.

(57) ABSTRACT

An endoscopic includes a handle, a tubular member, a control member, and an end effector assembly. The handle has a stationary member and a movable member. The movable member includes a constrained curved path for passage of the control member. The tubular member has an end coupled to the stationary member and a distal end rotatably coupled to the end effector assembly. The control member extends through the curved path, the tubular member, and is coupled to the end effector assembly. A knob is attached to the movable member and control member. Displacement of the movable member relative to the stationary member causes actuation of the end effector assembly, and rotation of the knob on the movable member causes the control member to rotate within both the constrained curved path and the tubular member, and results in rotation of the end effector assembly.

28 Claims, 4 Drawing Sheets

(56) References Cited

U.S. PATENT DOCUMENTS

| | | | |
|---|---|---|---|
| 6,090,108 | A | 7/2000 | McBrayer et al. |
| 6,416,505 | B1 | 7/2002 | Fleischman et al. |
| 6,569,105 | B1 | 5/2003 | Kortenbach et al. |
| 6,695,774 | B2 | 2/2004 | Hale et al. |
| 8,007,432 | B2 | 8/2011 | Vakharia et al. |
| 8,409,175 | B2 | 4/2013 | Lee et al. |
| 8,961,396 | B2 | 2/2015 | Azarbarzin et al. |
| 2007/0203483 | A1* | 8/2007 | Kim .................. A61B 18/1445 606/41 |
| 2013/0172828 | A1* | 7/2013 | Kappel ............ A61B 17/00234 604/272 |
| 2014/0005478 | A1 | 1/2014 | Kennedy, II et al. |
| 2014/0012075 | A1* | 1/2014 | Konstorum .......... A61B 1/0051 600/104 |

\* cited by examiner

ROTATABLE ENDOSCOPIC INSTRUMENT

BACKGROUND OF THE INVENTION

1. Field of the Invention

The present invention relates to surgical instruments. More particularly, the present invention relates to flexible instruments for insertion through a lumen into a patient.

2. State of the Art

Endoscopy is a minimally invasive medical procedure that assesses the interior of the human body using an endoscope. An endoscope generally consists of a rigid or flexible tube, an fiber optic illumination system to guide light provided by a light source through the tube of the endoscope in order to illuminate the organ or object under inspection, and a viewing system for collecting an image of the organ or object under inspection and for recording the image on an internal CCD device (video-endoscope) or for transmitting the image through the tube via a fiber optic bundle to an external video processor for viewing (fiber-endoscope). The endoscope can include one or more "working" channels (typically 2-4·mm in diameter) having a surgeon-accessible entry port through which specialized medical instruments can be passed into the working channels of the endoscope and into the field of view. Such specialized instruments (which can include graspers, biopsy forceps, scissors, etc.) can be used to grasp tissue, sample tissue for biopsy, or separate tissue, all from the inside of the body. Generally, due to the practicality of cleaning such small components, endoscopic instruments are designed to be single use instruments, and thereafter disposed.

Laparoscopy is a minimally invasive surgical technique in which operations in the abdomen or thorax are performed through small incisions (usually 0.5-1.5 cm) via a laparoscope. There are generally two types of laparoscopes, including a telescopic rod lens system that is usually connected to a video camera (single chip or three chip) and a digital laparoscope where the camera is placed at the end of the laparoscope, thus eliminating the rod lens system. A fiber optic cable system connected to a light source (halogen or xenon is inserted through a surgical port to illuminate the operative field for viewing. The abdomen is usually insufflated with carbon dioxide gas to create a working and viewing space. Specialized surgical instruments can be introduced into the abdomen or thorax through a surgical port in order to take biopsies and retrieve organs (or pieces thereof) and/or foreign objects from the inside of the body.

The surgical instruments used for endoscopy and laparoscopy generally include an end effector assembly mounted adjacent the distal end of a tube or coil. Handles are mounted to the proximal end of the tube or coil and move an actuator axially through the tube or coil. The distal end of the actuator is mechanically coupled to the end effector assembly in a manner that transforms the axial movement of the actuator into the desired movement of the end effector assembly.

In certain procedures, it may be advantageous to be able to additionally orient the end effector assembly toward a target location. One way to provide such orientation is provide a system that permits transmission of a rotational force from the proximal end of the instrument to the end effector assembly so that the end effector assembly is urged in rotation relative to the tube or coil. Various rotational systems have been proposed and implemented. However, such rotational systems have several disadvantages. First, is the complexity of their general structures. The additional structural requirements for the rotational system can result in an instrument that is too expensive for single use and disposal. Second, is a complexity of use of such system. Often such instruments are designed to require one hand to operate the handle to open and close the end effector assembly and the other hand to operate the handle to transmit the rotation force. Thus, use of the one instrument fully occupies the hands of the user. However, the user also is often responsible for controlling and manipulating the endoscope at the same time as the endoscopic instrument is used. An unworkable situation results.

SUMMARY OF THE INVENTION

An endoscopic instrument for manipulation of tissue in a patient includes a proximal handle assembly, a flexible tubular member, a flexible control member and an end effector assembly. The handle assembly has a stationary member and a movable member displaceable relative to the stationary member. The movable member includes a constrained curved path through which the control member passes and in which the control member is held. The tubular member has a proximal end coupled to the stationary member of the handle and a distal end rotatably coupled to the end effector assembly, and defines a longitudinal axis between its proximal and distal ends. The control member extends through the constrained curved path, the tubular member, and is coupled to the end effector assembly. A rotational input is attached to the proximal end of the control member. Movement of the movable member relative to the stationary member causes actuation of the end effector assembly, and rotation of the rotational input relative to the movable member causes the control member to rotate within both the constrained curved path and the tubular member, and results in rotation of the end effector assembly about the longitudinal axis. The actuation input and rotational input can both be operated by a single user's hand holding the handle assembly. Further, the rotation is highly accurate and the end effector assembly can be rotated even within a retroflexed endoscope.

DETAILED DESCRIPTION OF THE PREFERRED EMBODIMENTS

Figure 1:
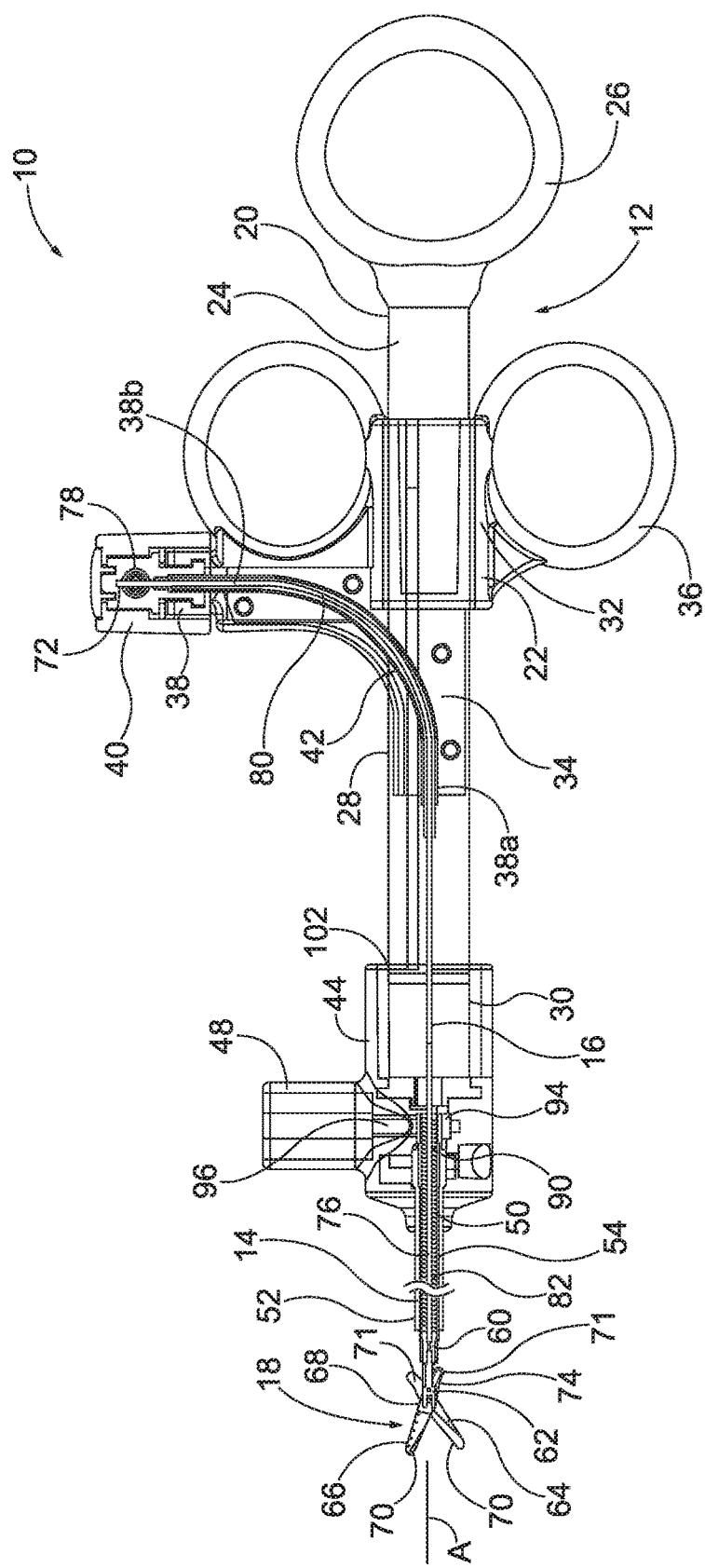
FIG. 1 is a broken longitudinal section view of an endoscopic instrument described herein.

Turning now to FIG. 1, an endoscopic instrument 10 for manipulation of tissue in a patient is shown. The endoscopic instrument 10 includes a proximal handle assembly 12, a flexible tubular member 14, a flexible control member 16 extending through the tubular member 14, and an end effector assembly 18 coupled to distal ends of the tubular member 14 and the control member 16. A longitudinal axis A of the instrument 10 is defined centrally through the tubular member 14. The longitudinal axis A is not meant to be limited to a straight line, as the tubular member may be curved within one or more planes, particularly when the instrument is inserted through the instrument channel of an endoscope that is subject to a curvature, including being retroflexed within the patient.

The handle assembly 12 has a stationary member 20 and a movable member 22. The stationary member 20 includes a shaft 24 having a proximal thumb ring 26, a longitudinal slot 28 and a distal portion 30. The movable member 22 includes an outer portion 32 mounted to the outside of the shaft 24, and an inner portion 34 that extends into the longitudinal slot 28. The outer portion 32 includes a pair of finger grips, preferably in the form of rings 36; brackets or other force receiving structure can alternatively be used. The outer portion also includes a mount 38 and a rotatable input 40 rotatably mounted at mount 38. The rotatable input 40 may be a knob, as shown, a lever, or another suitable input to apply a torque. The use of the rotatable input 40 is described below. The inner portion 34 includes a constrained curved path 42 extending from within the slot 28 to the outer portion 32. The constrained curved path is fixed in shape. The constrained curved path 42 may be molded within the movable member as a continuous lumen (as shown), may be defined by molded or received pins within the movable member, may be defined by a separate lumen such as formed by a curved metal hypotube, a plastic tube or a coil, or may be formed by any other structure that is capable of defining a constrained curved path through which the control member may be received and rotated in operation, as further described below. The curved path 38 preferably extends through a curve of 90°±20°, having a distal end 38a extending parallel, and preferably coaxial, with the longitudinal axis A and a proximal end 38b oriented transverse relative thereto. The movable member 22 is mounted to the shaft 24 such that the movable member 22 is longitudinally displaceable relative to the stationary member 20.

Figure 4:
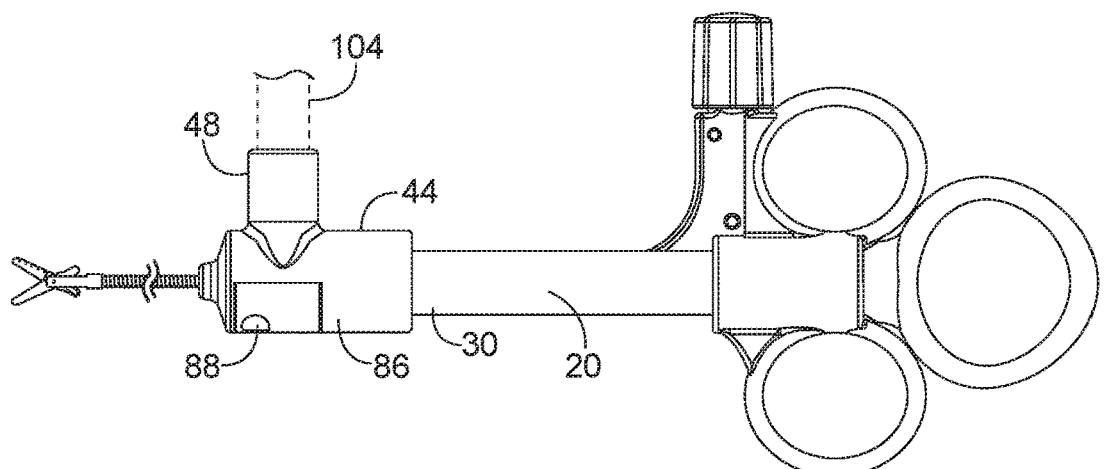
FIG. 4 is a side elevation view of the instrument with a cautery ferrule oriented in a first rotational orientation relative to the handle.
Figure 5:
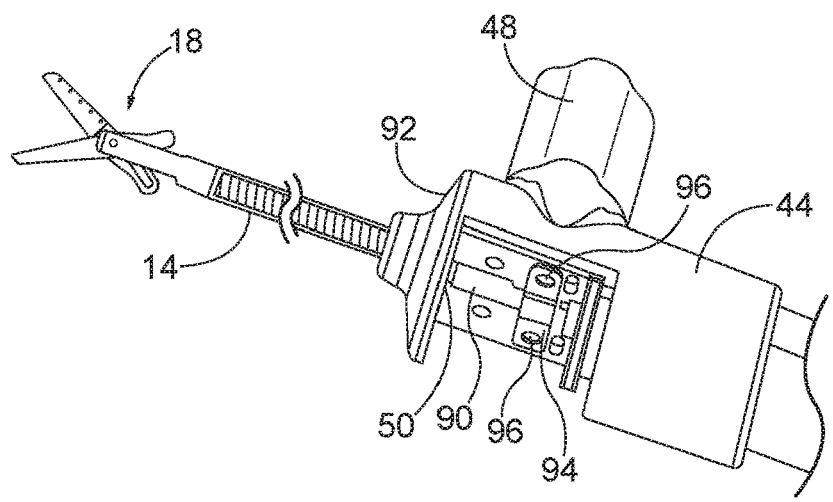
FIG. 5 is a broken, partial section of the instrument, illustrating the connection between the handle, the ferrule, and a flexible tubular member of the instrument.
Figure 6:
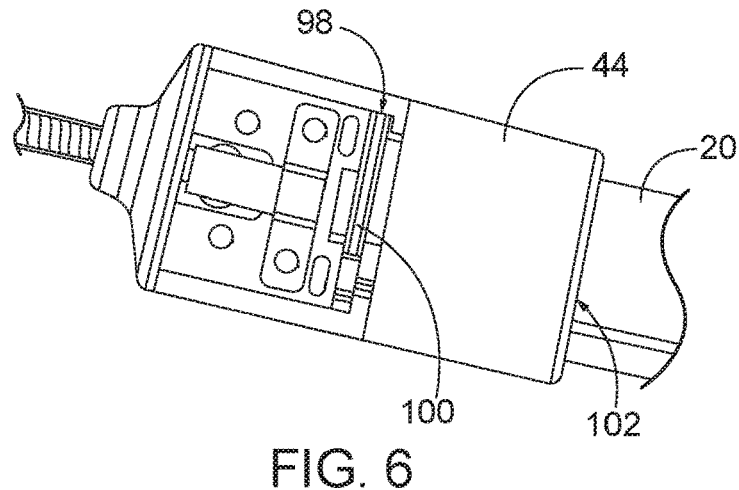
FIG. 6 is a broken, enlarged, partial section of the instrument, further illustrating the connection between the handle and the ferrule.
Figure 7:
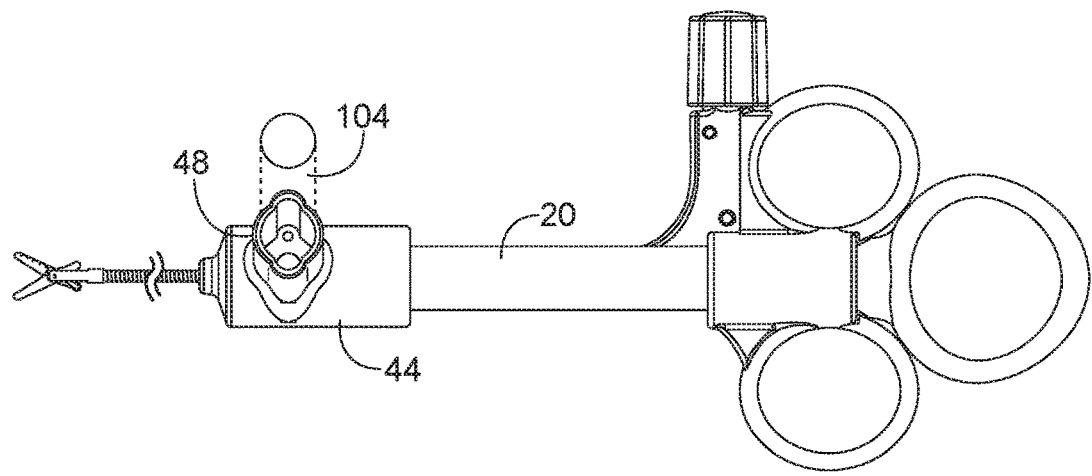
FIGS. 7 and 8 are side elevation views of the instrument with a cautery ferrule in respective second and third rotational orientations relative to the handle.
Figure 8:
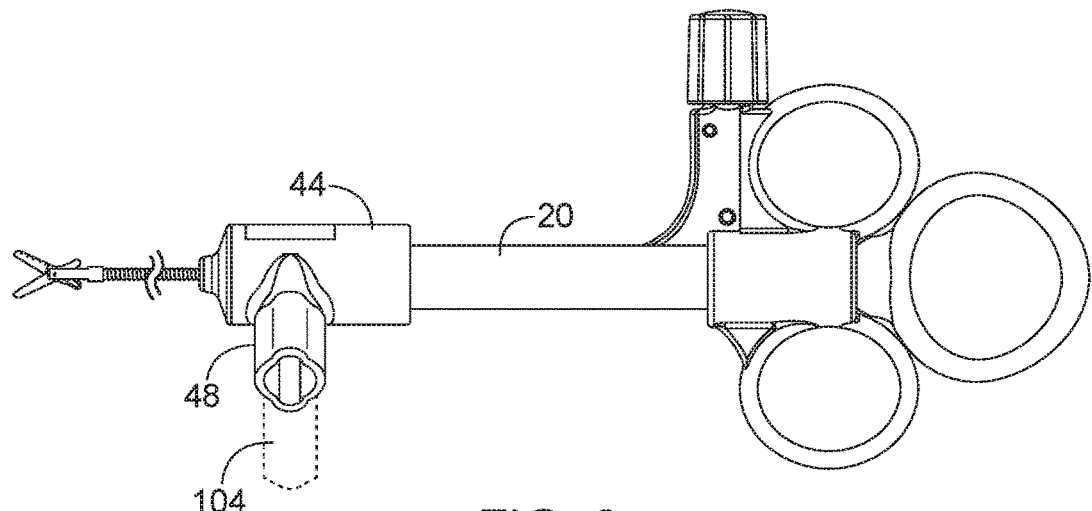

Turning now to FIG. 4, a ferrule 44 is rotatably coupled to the distal portion 30 of the stationary member 20. The ferrule 44 includes a first body portion 86 having a cautery connector 48, and a second cover portion 88, which when removed permits access to the inside of the ferrule 44 for assembly purposes, as shown at FIG. 5. A conductive metal sleeve 90 is fixed at a proximal end 50 of the tubular member 14. The metal sleeve 90 is retained in a throughbore 92 of the ferrule with a bracket 94 secured to the body portion 86 with screws 96 that extend into the connector 48. The screws 96, bracket 94, and metal sleeve 90 provide a conductive path from the connector 48 to the tubular member 14 and, in turn, the effector assembly 18. See also FIG. 1. Referring to FIG. 6, the ferrule 44 also includes a circumferential recess 98, and the distal end of the stationary member 20 includes a lip 100 that can be compressed into an open proximal end 102 of the ferrule 44 and released to expand into the recess 98 to rotatably couple the stationary member 20 relative to the ferrule 44. Shown in FIGS. 4, 7 and 8, as a result of the rotational coupling, when a cautery cable 104, extending to an energy source (not shown), is connected to the cautery connector 48, the ferrule 44 can be rotated for convenient positioning of the cable; i.e., so that the connector 48 and cable can be radially reoriented in any rotational direction toward the energy source and relative to the stationary member 20 without tangling about the instrument 10.

The tubular member 14 has a distal end 52 coupled to the end effector assembly 18. The tubular member 14 is preferably formed of a metal coil. A lubricious, insulative, flexible polymeric jacket 54 covers the metal coil. The tubular member is preferably sufficiently flexible to curve within the working channel of an endoscope extending within a tortuous path, such a retroflexed configuration.

The end effector assembly 18 includes a clevis 62 rotatably mounted on a plane bearing 60 to the distal end 52 of the tubular member, and at least one end effector 64 mounted for movement on the clevis 62. In the shown embodiment, the end effector assembly 18 includes first and second end effectors 64, 66 rotatably coupled to the clevis 62 at a pin 68. The end effectors 64, 66 are scissors having distal cutting blades 70 and proximal tangs 71. In a well-known actuation mechanism, the tangs 71 each include a cam slot (not shown).

The control member 16 has a proximal end 72 and a distal end 74. The distal end 74 has a cam pin (not shown) that rides within the cam slots of the end effectors 64, 66 such that longitudinal displacement of the cam pin relative to the cam slot results in actuation of the end effector assembly 18. A central portion 76 of the control member 16 extends within the tubular member 14. The proximal end 72 of the control member extends through the constrained curved path 38 to the rotatable input 40. A set screw 78 is preferably used to fix the proximal end 72 of the control member 16 to the input 40. The control member 16 is constructed to not exceed its elastic limit within the constrained curved path, and thereby assumes no plastic deformation under the forces to which it can be subject by the handle assembly; that is, the control member does not take a set. The control member 16 is preferably a single strand wire, and also preferably made of nickel titanium alloy, a stainless steel alloy, or other suitable elastic or superelastic alloy. Alternatively, the control member 16 may be a plurality of wires. In addition, the control member 16 may be a suitable cable or braid construction meeting the requirements herein.

A low-friction first bearing 80 is preferably located radially between the control member 16 and the curved path 38. The first bearing 80 may be loosely positioned between the control member 16 and the constrained curved path 38 such that it is free floating in the radial space therebetween. The first bearing 80 may alternatively be coated onto or permanently affixed to the control member 16. As yet another alternative, the first bearing 80 may be defined by a material within or coated on the lumen of the curved path 38 or may be a supplemental tube of suitable low friction material permanently positioned with the curved path. Exemplar bearing surface materials includes polytetrafluoroethylene (PTFE) and polyethylene.

A polymeric tubular second bearing 82 may also be provided radially between the tubular member 14 and the control member 16 to take up the space between the two elements and prevent buckling of the control member 16 when the instrument 10 is flexed.

Figure 2:
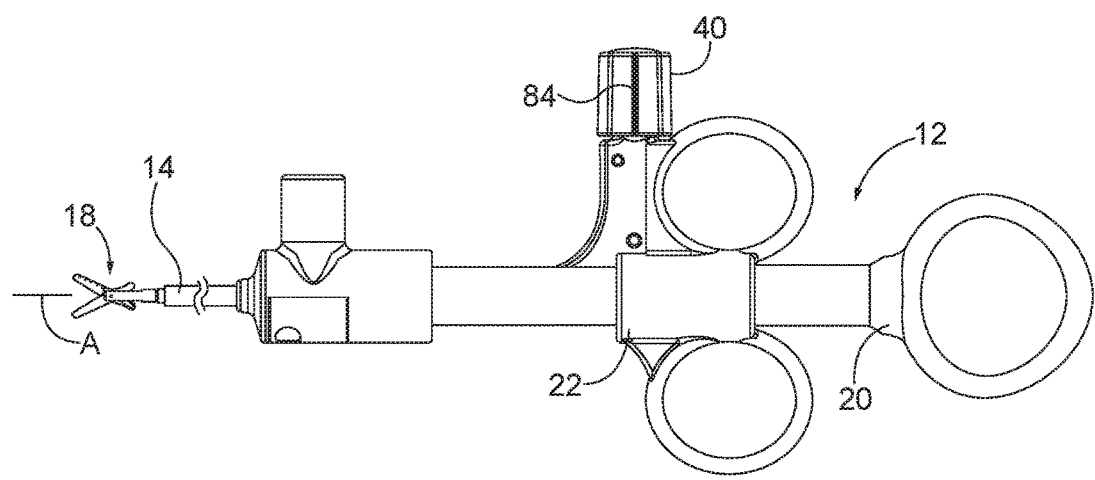
FIG. 2 is a broken view of the instrument with the handle operated such that the end effector assembly is open and in a first rotational orientation.
Figure 3:
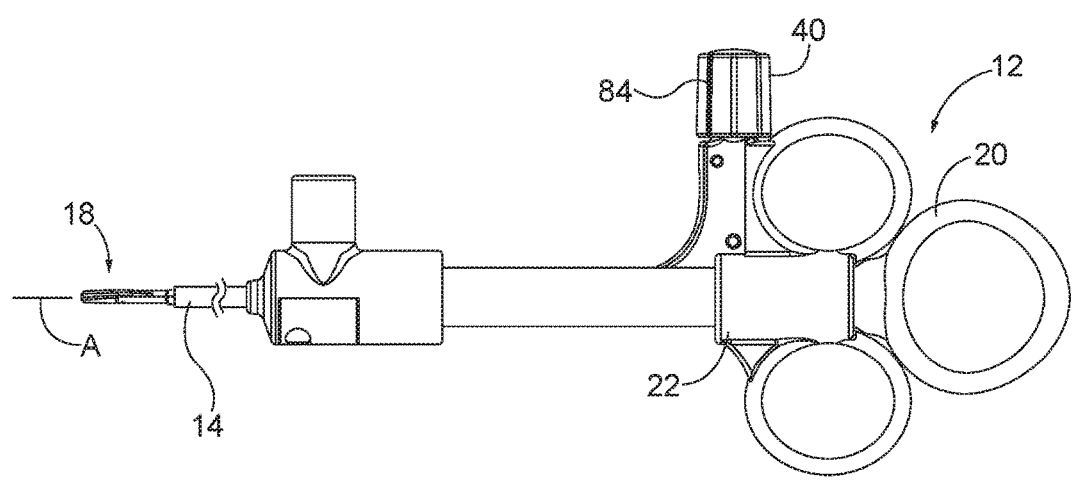
FIG. 3 is a broken view of the instrument with the handle operated such that the end effector assembly is closed and in a second rotational orientation.

Turning now to FIG. 2, when the movable member 22 of the handle assembly 12 is distally advanced on the stationary member 20, the control member 16 (not shown) is longitudinally advanced within the tubular member 14. This results in actuation of the end effector assembly 18 to an open position. Then, as shown in FIG. 3, when the movable member 22 of the handle assembly 12 is proximally retracted on the stationary member 20, the control member 16 is longitudinally withdrawn within the tubular member 14 to actuate the end effector assembly 18 into a closed position.

In either the open (movable member distally advanced) or closed (movable member proximally retracted) positions, the knob 40 may be rotated on the movable member 22. Indicia 84 are preferably provided to indicate a reference orientation. Alternatively, the shape of the knob may be radially non-uniform to identify directionality. Rotation of the knob 40 relative to the movable member 22 causes the control member 16 fixed thereto to rotate within both the constrained curved path 38 and the tubular member 14, and results in controlled rotation of the end effector assembly 18 about the longitudinal axis A. FIG. 2 shows the knob 40 and end effector assembly 18 in a first rotational orientation. FIG. 3 shows both the knob 40 and end effector assembly 18 in a second rotational orientation offset from the first rotational orientation. More specifically, FIG. 3 shows the knob rotated 45°, and the end effector assembly likewise rotated 45°. Thus, there is a one to one correspondence between the degree of rotation of the knob 40 and the resultant rotation of the end effector assembly 18. The construction of the control member 16 prevents any whip of rotation and kinking. The first and second bearings 80, 82 further provide for smooth rotation; with tolerance control and a low friction environment. Because the knob 40 is located on the movable member 22, the actuation input for the end effector assembly 18 and rotational input to rotate the end effector assembly 18 about the longitudinal axis A can both be operated by a single hand of a user holding the handle assembly 12. Further, the rotation is accurate and the end effector assembly 18 can be rotated even within a retroflexed endoscope.

In accord with the design, the knob 40, control member 16, and the end effector assembly 18 have a first rotational action, and the ferrule 44, bracket 94, sleeve 90, and coil 14 have a second rotational action distinct and separate from the first rotational action.

There have been described and illustrated embodiments of a rotatable instrument. While particular embodiments of the instrument have been described, it is not intended that the invention be limited thereto, as it is intended that the invention be as broad in scope as the art will allow and that the specification be read likewise. The terms endoscopic surgical instruments or endoscopic instruments is used herein to refer to both endoscopic and laparoscopic surgical instruments, and endoscopes as used herein refers collectively to endoscopes and laparoscopes. The general principles discussed herein apply to most endoscopic instruments, but it is recognized that specific endoscopic instruments differ in length, size, stiffness, as well as other characteristics as the instruments are typically designed for a particular application as such instruments can be used for a wide variety of minimally invasive surgical procedures. While the instrument has been described with respect to an exemplar end effector assembly including scissors blades, it is intended that any endoscopic end effector assembly benefiting from rotational orientation be included herein. By way of example only, forceps, clamps, retractors, clip appliers jaws, can also be provided as a part of the end effector assembly. Also, while a cam-pin and slot assembly has been disclosed for actuating the end effector assembly, other known actuation mechanisms including push/pull wires connecting to the end effector tangs, spring biased and cammed end effector assemblies, and other systems for actuating the end effector assembly between open and closed positions can be used. It will therefore be appreciated by those skilled in the art that yet other modifications could be made to the provided invention without deviating from its scope as claimed.

What is claimed is:

1. An endoscopic instrument for manipulation of a tissue in a patient, comprising:
   a) a proximal handle having a stationary member and a movable member movable relative to the stationary member;
   b) a non-straight constrained curved path provided in the movable member of the proximal handle;
   c) a flexible tubular member having a proximal end and distal end and defining a longitudinal axis therebetween, the proximal end longitudinally fixed relative to the stationary member;
   d) an end effector assembly rotatably coupled to the distal end of the flexible tubular member, the end effector assembly having a first member and a second member movable relative to the first member to manipulate the tissue;
   e) a flexible control member having a proximal end and a distal end, the control member extending through the constrained curved path in the movable member, through the tubular member, and coupled to the end effector assembly, the control member held within an elastic bend through the constrained curved path; and
   f) a rotational input attached to the proximal end of the control member and mounted on the movable member of the proximal handle, the rotational input rotatable about an axis transverse to the longitudinal axis,
      wherein movement of the movable member relative to the stationary member causes actuation of the end effector assembly, and
      wherein rotation of the rotational input relative to the movable member causes the control member to rotate within the constrained curved path and the tubular member and results in rotation of the end effector assembly about the longitudinal axis.

2. The endoscopic instrument according to claim 1, wherein:
   the movable member is longitudinally displaceable relative to the stationary member.

3. The endoscopic instrument according to claim 1, wherein:
   the constrained curved path has a first end and a second end, the first end extends parallel to the longitudinal axis and the second end extends transverse to the longitudinal axis.

4. The endoscopic instrument according to claim 1, wherein:
   the constrained curved path extends through an arc of 90°±20°.

5. The endoscopic instrument according to claim 1, wherein:
   the constrained curved path has a first end coaxial with proximal end of the tubular member.

6. The endoscopic instrument according to claim 1, wherein:
   the constrained curved path is molded into the movable member.

7. The endoscopic instrument according to claim 1, wherein:
   the constrained curved path is a lumen provided within the movable member.

8. The endoscopic instrument according to claim 1, wherein:
   the constrained curved path comprises a curved tube.

9. The endoscopic instrument according to claim 8, wherein:
the curved tube is a metal hypotube, a plastic tube, or a coil.

10. The endoscopic instrument according to claim 1, wherein:
the control member is a flexible elastic wire.

11. The endoscopic instrument according to claim 10, wherein:
the flexible wire is structured to prevent plastic deformation under forces imposed by the handle assembly.

12. The endoscopic instrument according to claim 10, wherein:
the flexible wire is comprised of nickel titanium alloy or stainless steel.

13. The endoscopic instrument according to claim 10, wherein:
the flexible wire is comprised of an elastic or superelastic alloy.

14. The endoscopic instrument according to claim 1, wherein:
the control member comprises a member selected from a group consisting of a plurality of wires, a wire cable, and a braid of wires.

15. The endoscopic instrument according to claim 1, wherein:
the rotational input is a knob rotatably coupled to the movable member of the handle assembly.

16. The endoscopic instrument according to claim 1, further comprising:
a bearing located radially between the control member and the constrained path.

17. The endoscopic instrument according to claim 16, wherein:
the bearing is loosely provided between the control member and the constrained curved path.

18. The endoscopic instrument according to claim 16, wherein:
the bearing is coated onto or otherwise attached to the control member.

19. The endoscopic instrument according to claim 16, wherein:
the bearing is located within a lumen of the constrained curved path.

20. The endoscopic instrument according to claim 1, wherein:
the first and second members of the end effector assembly are scissors blades.

21. An endoscopic instrument for manipulation of a tissue in a patient, comprising:
a) a handle assembly including a stationary member and a movable member movable relative to the stationary member, the movable member defining a non-straight constrained curved path;
b) a flexible tubular member having a proximal end and distal end, the proximal end longitudinally fixed relative to the stationary member of the handle assembly;
c) an end effector assembly rotatably coupled to the distal end of the flexible tubular member;
d) a flexible control member having a proximal end, a distal end, and a longitudinal axis extending between the proximal and distal ends, the control member extending through the constrained curved path and the tubular member to the end effector assembly, the control member assuming a bend through the constrained curved path within an elastic limit of the control member such that the control member is not subject to plastic deformation by the bend; and
e) a rotational input attached to the proximal end of the control member, the rotational input rotatable about an input axis transverse to the longitudinal axis,
wherein actuation of the handle assembly longitudinally displaces the control member relative to the tubular member to operate the end effector assembly, and
wherein rotation of the rotational input about the input axis relative to the movable member of the handle assembly causes the control member to rotate around the longitudinal axis and within the constrained curved path and within the elastic limit of the control member, and results in rotation of the end effector assembly relative to the tubular member.

22. The endoscopic instrument according to claim 21, wherein:
the control member is a nickel titanium alloy.

23. The endoscopic instrument according to claim 21, wherein:
the constrained curved path extends through an arc of 90°±20°.

24. The endoscopic instrument according to claim 21, wherein:
actuation of the handle assembly longitudinally displaces the control member relative to the flexible tubular member.

25. The endoscopic instrument according to claim 21, wherein:
the end effector assembly has a first member and a second member movable relative to the first member upon actuation of the handle assembly to manipulate the tissue.

26. An endoscopic instrument for manipulation of a tissue in a patient, comprising:
a) a proximal handle having a stationary member and a movable member movable relative to the stationary member, the stationary member having a distal end;
b) a ferrule rotatably positioned at the distal end of the stationary member, the ferrule having an integrated cautery connector with an electrode and defining a throughbore;
c) a flexible tubular member having a proximal end and a distal end and defining a longitudinal axis therebetween, the proximal end extending from the ferrule and longitudinally fixed relative to the stationary member;
d) an end effector assembly rotatably coupled to the distal end of the flexible tubular member;
e) a flexible control member having a proximal end and a distal end, the control member extending through the ferrule, the tubular member, and attached to the end effector assembly; and
f) a rotational input attached to the proximal end of the control member and rotationally mounted on the movable member, the rotational input rotatable about an axis transverse to the longitudinal axis,
wherein movement of the movable member relative to the stationary member causes actuation of the end effector assembly,
wherein rotation of the ferrule relative to the stationary member radially reorients the cautery connector, and
wherein rotation of the rotational input relative to the movable member causes the control member to rotate and results in rotation of the end effector assembly about the longitudinal axis.

27. The endoscopic instrument of claim 26, wherein:
a conductive metal sleeve is fixed to the proximal end of the tubular member, a metal bracket surrounds a portion of the sleeve, and conductive fasteners secure the bracket relative to the ferrule and extend into the cautery connector.

28. An endoscopic instrument for manipulation of a tissue in a patient, comprising:
  a) a proximal handle having a stationary member and a movable member movable relative to the stationary member, the stationary member having a distal end;
  b) a ferrule integrated with the instrument in a rotatable manner at the distal end of the stationary member, the ferrule having a cautery connector with an electrode;
  c) a flexible tubular member having a proximal end and distal end and defining a longitudinal axis therebetween, the tubular member longitudinally fixed relative to the stationary member;
  d) a metal sleeve fixed at the proximal end of the tubular member;
  e) a bracket retaining the sleeve relative to the ferrule;
  f) an end effector assembly rotatably coupled to the distal end of the flexible tubular member;
  g) a flexible control member having a proximal end and a distal end, the control member extending through the ferrule, the tubular member, and coupled to the end effector assembly; and
  h) a rotational input attached to the proximal end of the control member and rotationally mounted on the movable member, wherein
    the rotational input, the control member, and the end effector assembly have a first rotational action,
    the ferrule, bracket, sleeve, and flexible tubular member have a second rotational action distinct and separate from the first rotational action, and
    the flexible tubular member extends along a first axis, and the rotational input rotates about a second axis transverse to the first axis.

* * * * *